(12) United States Patent
Yamaguchi et al.

(10) Patent No.: US 6,930,778 B2
(45) Date of Patent: Aug. 16, 2005

(54) MICROCHEMICAL SYSTEM

(75) Inventors: Jun Yamaguchi, Tokyo (JP); Akihiko Hattori, Osaka (JP); Takehiko Kitamori, Tokyo (JP); Manabu Tokeshi, Kanagawa (JP)

(73) Assignees: Nippon Sheet Glass Co., Ltd., Osaka (JP); Kanagawa Academy of Science & Technology, Kawasaki (JP)

( * ) Notice: Subject to any disclaimer, the term of this patent is extended or adjusted under 35 U.S.C. 154(b) by 0 days.

(21) Appl. No.: 10/733,491

(22) Filed: Dec. 10, 2003

(65) Prior Publication Data

US 2004/0233449 A1 Nov. 25, 2004

Related U.S. Application Data

(63) Continuation of application No. PCT/JP02/05693, filed on Jun. 7, 2002.

(30) Foreign Application Priority Data

Jun. 12, 2001 (JP) ........................................ 2001-177294

(51) Int. Cl.⁷ .............................................. G01N 21/00
(52) U.S. Cl. ..................................... 356/432; 356/442
(58) Field of Search ............................... 356/432, 442, 356/317, 319, 430; 359/288, 244, 289, 299, 350

(56) References Cited

U.S. PATENT DOCUMENTS

| 4,927,268 A | * | 5/1990 | Carr et al. ................... 356/336 |
| 4,938,593 A | * | 7/1990 | Morris et al. ................ 356/344 |
| 5,513,006 A | * | 4/1996 | Schulz et al. ................ 356/432 |
| 6,452,710 B1 | * | 9/2002 | Hiraga et al. ................ 359/244 |

FOREIGN PATENT DOCUMENTS

| JP | 61-255308 A | 11/1986 |
| JP | 2000-2677 A | 1/2000 |
| JP | 2001-59829 A | 3/2001 |

* cited by examiner

Primary Examiner—Layla Lauchman
(74) Attorney, Agent, or Firm—Frishauf, Holtz, Goodman & Chick, P.C.

(57) ABSTRACT

A microchemical system is provided, which can improve the working efficiency of the user and can be designed compact in size. The microchemical system is provided with an optical fiber 10 with a gradient index rod lens 102 mounted on an end thereof. The lens-possessing optical fiber 10 is comprised of an optical fiber 101 that transmits exciting light and detecting light in the single mode, and a ferrule 103 for expanding the outer diameter of the optical fiber 101 to the same value as that of the gradient index rod lens 102. The gradient index rod lens 102 and the optical fiber 101 are rigidly joined together by means of a sleeve 104.

12 Claims, 10 Drawing Sheets

MICROCHEMICAL SYSTEM

This application is a Continuation Application of International Application PCT/JP02/05693 filed Jun. 7, 2002.

TECHNICAL FIELD

The present invention relates to a microchemical system that performs a photothermal conversion spectroscopic analysis method of generating a thermal lens by convergently irradiating a sample with exciting light to measure detecting light passing through the thermal lens, and more particularly to a microchemical system that is capable of performing analysis of very small amounts of samples in measurements in very small spaces and can be suitably used for desk thermal lens microscopes.

BACKGROUND ART

Conventionally, in consideration of the rapidity of chemical reactions, and the need to carry out reactions using very small amounts, on-site analysis and the like, integration technology for carrying out chemical reactions in very small spaces has been focused upon, and research into this technology has been carried out with vigor throughout the world.

Microchemical systems that use glass substrates or the like are an example of such integration technology for carrying out chemical reactions. Such a microchemical system is intended to have capability of carrying out all functions of mixing, reaction, separation, extraction, detection or the like on a sample placed in a very narrow channel which is formed in a small glass substrate or the like. Examples of reactions carried out in the microchemical system include diazotization reactions, nitration reactions, and antigen-antibody reactions. Examples of extraction/separation include solvent extraction, electrophoretic separation, and column separation.

As an example in which 'separation' is the sole aim, an electrophoresis apparatus for analyzing extremely small amounts of proteins, nucleic acids or the like has been proposed by Japanese Laid-open Patent Publication (Kokai) No. 8-178897. This electrophoresis apparatus analyzes extremely small amounts of proteins, nucleic acids or the like and is provided with a channel-formed plate-shaped element comprised of two glass substrates joined together. Because the element is plate-shaped, breakage is less likely to occur than in the case of a glass capillary tube having a circular or rectangular cross section, and hence handling is easier.

In these microchemical systems, because the amount of the sample is very small, a high-precision detection method is essential. The path to making a detection method of the required precision fit for practical use has been opened up through the establishment of a photothermal conversion spectroscopic analysis method which utilizes a thermal lens effect that is produced through a liquid-borne sample absorbing light in a very narrow channel.

The photothermal conversion spectroscopic analysis method utilizes a photothermal conversion effect that when light is convergently irradiated onto a sample, the temperature of a solvent is locally increased by thermal energy emitted due to light absorbed by a solute in the sample to cause a change in the refractive index and hence generate a thermal lens.

FIG. 7 is a view useful in explaining the principle of a thermal lens.

In FIG. 7, a convergent beam of exciting light is irradiated onto an extremely small sample via an objective lens of a microscope, whereupon the photothermal conversion effect described above takes place. For most substances, the refractive index drops as the temperature rises, and hence the drop rate of the refractive index of the sample is greater toward the center of the convergent beam of exciting light, which is where the temperature rise is highest. Due to thermal diffusion, the temperature rise becomes smaller and hence the drop in refractive index becomes smaller, with increasing distance from the center of the convergent beam of exciting light, i.e. decreasing distance to the periphery of the same. Optically, this pattern of change in the refractive index brings about the same effect as with a concave lens, and hence the effect is called the thermal lens effect. The size of the thermal lens effect, i.e. the power of the thermal lens is proportional to the optical absorbance of the sample. Moreover, in the case that the refractive index increases with temperature, a converse effect to the above, i.e. the same effect as a convex lens is produced.

In the photothermal conversion spectroscopic analysis method described above, thermal diffusion in a sample, i.e. change in refractive index of the sample, is observed, and hence the method is suitable for detecting concentrations in extremely small amounts of samples.

A photothermal conversion spectroscopic analyzer has been proposed by Japanese Laid-open Patent Publication (Kokai) No. 10-232210 as a microchemical system that uses the photothermal conversion spectroscopic analysis method described above.

In the conventional photothermal conversion spectroscopic analyzer, a channel-formed plate-shaped element is disposed below the objective lens of a microscope, and exciting light of a predetermined wavelength outputted from an exciting light source is introduced into the microscope. The exciting light is thus convergently irradiated via the objective lens onto a sample in the analysis channel of the channel-formed plate-shaped element. Thus, a thermal lens is formed about the convergent irradiation position in which the exciting light is convergently irradiated.

Moreover, detecting light having a wavelength different to that of the exciting light is outputted from a detecting light source and also introduced into the microscope and then emitted therefrom. The detecting light emitted from the microscope is convergently irradiated onto the thermal lens that has been formed in the sample by the exciting light. Then, the detecting light passing through the sample is either diverged or converged due to the effect of the thermal lens. The diverged or converged light exiting the sample passes as signal light through a converging lens and a filter or just a filter, and is then received and detected by a detector. The intensity of the detected signal light depends on the refractive index of the thermal lens formed in the sample. The detecting light may have the same wavelength as that of the exciting light, or the exciting light may be used as the detecting light as well.

In the spectroscopic analyzer described above, a thermal lens is thus formed at the convergent irradiation position (hereinafter referred to as "the focal position") of the exciting light, and the change in refractive index within the formed thermal lens is detected by means of detecting light.

In most cases where the photothermal conversion spectroscopic analysis method using the thermal lens described above is carried out, it is required that the focal position of the exciting light and that of the detecting light should be different from each other. FIGS. 8A and 8B are views useful in explaining the formation position of the thermal lens and the focal position of the detecting light in the direction of travel of the exciting light. FIG. 8A shows a case in which the objective lens has chromatic aberration, whereas FIG. 8B shows a case in which the objective lens does not have chromatic aberration.

In the case that the objective lens 130 has chromatic aberration, a thermal lens 131 is formed at the focal position 132 of the exciting light as shown in FIG. 8A. The focal position 133 of the detecting light is shifted by an amount ΔL from the focal position 132 of the exciting light, and thus changes in the refractive index within the thermal lens 131 can be detected as changes in the focal distance of the detecting light from the detecting light. In the case that the objective lens 130 does not have chromatic aberration, on the other hand, the focal position 133 of the detecting light is almost exactly the same as the focal position 132 of the exciting light, i.e. the position of the thermal lens 131 as shown in FIG. 8B. The detecting light is thus not deflected by the thermal lens 131, and hence changes in the refractive index within the thermal lens 131 cannot be detected.

However, the objective lens of a microscope is generally manufactured so as not to have chromatic aberration, and hence the focal position 133 of the detecting light is almost exactly the same as the position of the thermal lens 131 formed at the focal position 132 of the exciting light as described above, as shown in FIG. 8B. Changes in the refractive index within the thermal lens 131 thus cannot be detected. There is thus a problem that trouble must be taken to either shift the position in which the thermal lens 131 is formed from the focal position 133 of the detecting light every time a measurement is taken as shown in FIGS. 9A and 9B, or else angle the detecting light slightly using a lens (not shown) before passing the detecting light through the objective lens 130 so that the focal position 133 of the detecting light will be shifted from the thermal lens 131 as shown in FIG. 10. This also leads to degraded working efficiency of the user.

It is an object of the present invention to provide a microchemical system which enables working efficiency of the user to be improved and can be made smaller in size.

DISCLOSURE OF INVENTION

To attain the above object, in a first aspect of the present invention, there is provided a microchemical system that convergently irradiates exciting light and detecting light onto a sample using a converging lens, and measures the detecting light passing through a thermal lens generated by the convergent irradiation of the exciting light, characterized by comprising an optical fiber for guiding the exciting light and the detecting light to the converging lens.

In the first aspect, it is preferable that the converging lens is secured to one of both ends of the optical fiber that is closer to the sample.

In the first aspect, it is preferable that the optical fiber comprises a single optical fiber.

In the first aspect, it is preferable that the exciting light and the detecting light have respective different frequencies, the converging lens has chromatic aberration, and the exciting light and the detecting light passing through the converging lens have respective different focal positions.

In the first aspect, it is preferable that the converging lens is a gradient index lens.

In the first aspect, it is preferable that the gradient index lens is a rod lens.

In the first aspect, it is preferable that the optical fiber exhibits a single mode in the frequencies of the exciting light and the detecting light.

In the first aspect, it is preferable that the microchemical system comprises moving means for moving the optical fiber having the converging lens secured to the one end thereof.

In the first aspect, it is preferable that the microchemical system comprises at least two pairs of the optical fiber and the converging lens secured to the one end of the optical fiber.

BRIEF DESCRIPTION OF DRAWINGS

FIG. 8A shows a case in which the objective lens has chromatic aberration;

FIG. 8B shows a case in which the objective lens does not have chromatic aberration;

FIG. 9A shows a case in which the thermal lens is formed at a side close to the objective lens with respect to the focal position of the detecting light;

FIG. 9B shows a case in which the thermal lens is formed at a side remote from the objective lens with respect to the focal position of the detecting light.

BEST MODE OF CARRYING OUT THE INVENTION

Embodiments of the microchemical system according to the present invention will now be described with reference to the drawings.

Figure 1:
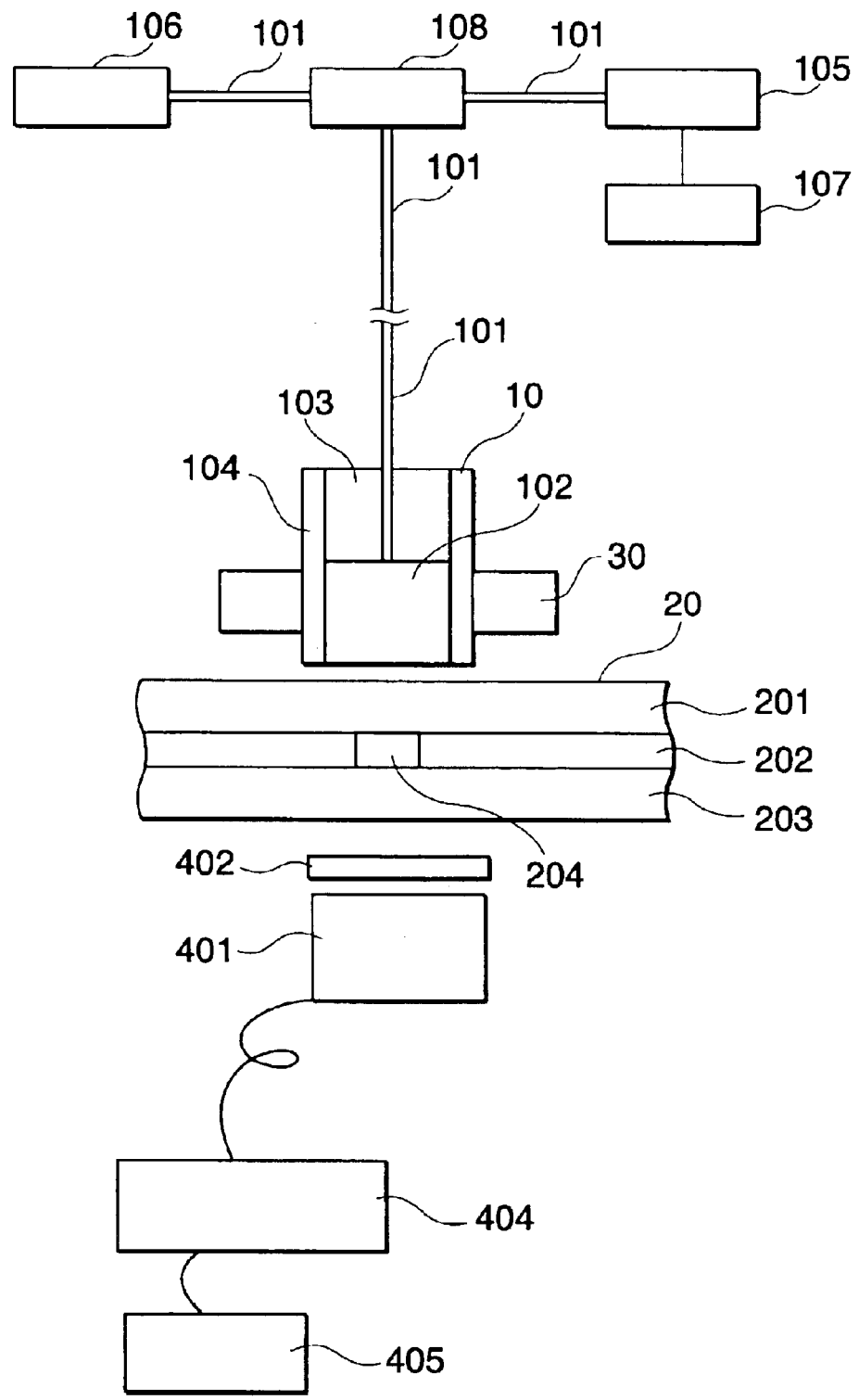
FIG. 1 is a schematic view showing the constitution of a microchemical system according to a first embodiment of the present invention.

FIG. 1 is a schematic view showing the constitution of a microchemical system according to a first embodiment of the present invention.

In FIG. 1, an optical fiber 10 with a lens mounted on an end thereof (hereinafter referred to as "the lens-possessing optical fiber 10") is mounted on an end of an optical fiber 101 that transmits exciting light and detecting light in the single mode. The lens-possessing optical fiber 10 is comprised of a gradient index rod lens 102, and a ferrule 103 for expanding the outer diameter of the optical fiber 101 to substantially the same value as that of the gradient index rod lens 102. The gradient index rod lens 102 is disposed in an optical paths for the exciting light and the detecting light at a location downstream of the ferrule 103 in the direction of travel of the exciting light and the detecting light. The gradient index rod lens 102 and the optical fiber 101 are rigidly joined together by means of a sleeve 104. The optical fiber 101 and the gradient index rod lens 102 may be held in tight contact with each other or in spaced relation to each other.

The optical fiber 101 is bifurcated into two branches at the other end thereof with an optical multiplexer 108 mounted thereon, and an exciting light source 105 is disposed at an end of one of the branches, and a detecting light source 106 is disposed at an end of the other branch. Connected to the exciting light source 105 is a modulator 107 for modulating the exciting light. The exciting light and the probe light incident on the optical fiber are multiplexed by the wavelength multiplexer 108. It should be noted that, instead of using the optical multiplexer 108, a dichroic mirror or the like may be used to coaxially align the exciting light and the detecting light and introduce the resulting coaxial light into the optical fiber 101.

A plate-shaped element 20 in which a sample to be detected is made to flow is comprised of glass substrates 201, 202 and 203 which are stacked upon one another in three layers. The intermediate glass substrate 202 is formed therein with a channel 204 for mixing, agitating, synthesizing, separating, extracting or detecting a sample.

The plate-shaped element 20 is preferably made of glass in terms of durability and chemical resistance. In the case where living body samples such as cell samples are used for example for DNA analysis, the material of the glass substrates 201 to 203 is preferably a glass that has excellent acid resistance and alkali resistance, for example a borosilicate glass, a soda lime glass, an aluminoborosilicate glass, a quartz glass or the like. However, the plate-shaped element 20 may be made of an organic material such as a plastic for some specific usage.

The lens-possessing optical fiber 10 is fixed in opposed relation to the channel 204 of the channel-formed plate-shaped element 20 by means of a jig 30.

A photoelectric transducer 401 for detecting the detecting light and a wavelength filter 402 that separates the exciting light and the detecting light from each other and selectively passes only the detecting light are disposed in opposed relation to the channel 204 at a location opposite to the lens-possessing optical fiber 10 with respect to the channel-formed plate-shaped element 20. A pin hole for allowing only part of the detecting light to pass may be provided at a location upstream of the photoelectric transducer 401 in the optical path for the detecting light. An output signal from the photoelectric transducer 401 is delivered to a lock-in amplifier 404 for synchronization with the modulator 107, and then analyzed by a computer 405.

An adhesive may be used to join together the glass substrates 201, 202 and 203, which is comprised, for example, of an organic adhesive including an acrylic or epoxy adhesive such as an ultraviolet curing type, a thermosetting type, and a two-part hardening type, or an inorganic adhesive. The glass substrates 201 to 203 may be thermally bonded together instead of using an adhesive.

The gradient index rod lens 102 is made of a cylindrical transparent element which has a refractive index continuously varying from the center to the periphery thereof and which is known as a converging light-transmitting body for which the refractive index n(r) at a position a distance r from the central axis in the radial direction is given approximately by the quadratic equation in r, $$n(r)=n_0\{1-(g^2/2^-)\cdot r^2\},$$

wherein no represents the refractive index at the central axis, and g represents the square distribution constant.

If the length $z_0$ of the rod lens 102 is chosen to be in a range of $0<z_0<\pi/2$ g, then the image formation characteristics of the rod lens 102 will be the same as those of a normal convex lens, even though the both end faces of the rod lens 102 are flat; when a parallel light beam is incident on one end face of the rod lens 102, a focal point will be formed at a position a distance $s_0$ from the other end face of the rod lens 102 (the end face from which the light beam exits), where $$s_0=cot(gz_0)/n_0g.$$

The rod lens 102 may be manufactured, for example, by the following method.

A rod-shaped element is formed from a glass having 57 to 63 mol % of $SiO_2$, 17 to 23 mol % of $B_2O_3$, 5 to 17 mol % of $Na_2O$, and 3 to 15 mol % of $Tl_2O$ as principal components. This glass rod element is then treated in an ion exchange medium such as a potassium nitrate salt bath, thus carrying out ion exchange between thallium ions and sodium ions in the glass and potassium ions in the medium, and hence giving the glass rod element a refractive index distribution in which the refractive index decreases continuously from the center of the glass rod element toward the periphery thereof.

In the microchemical system according to the first embodiment of the present invention, the rod lens 102 is mounted on a tip of the optical fiber 101 that transmits the exciting light and the detecting light, it is not necessary to adjust the optical paths for the exciting light and the detecting light and the optical axis of the rod lens 102 for each measurement, and no jig and solid surface table are required to align the optical axis. As a result, the microchemical system can be designed compact in size.

The focal position of the exciting light obtained by the rod lens 102 is required to be located in the channel 204 of the channel-formed plate-shaped element 20. Although the rod lens 102 need not be in contact with the channel-formed plate-shaped element 20, if it is in contact with the latter, the focal distance of the rod lens 102 can be adjusted utilizing the thickness of the upper glass substrate 201. If the thickness of the upper substrate 201 is insufficient, a spacer may be inserted between the rod lens 102 and the upper substrate 201. In these cases, the adjustment of the focal distance is also unnecessary, enabling designing the microchemical system more compact in size.

Figure 8A:
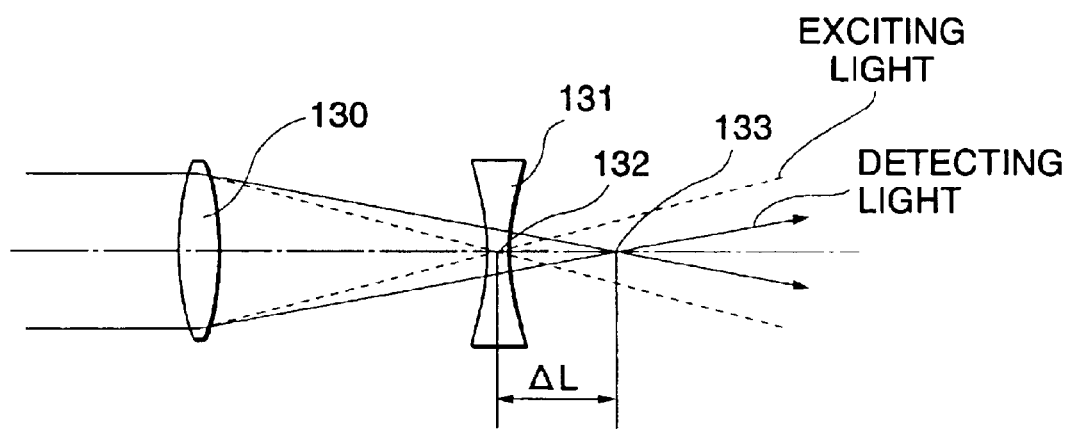
FIGS. 8A and 8B are views useful in explaining the formation position of a thermal lens and the focal position of detecting light in the direction of travel of exciting light; specifically.
Figure 8B:
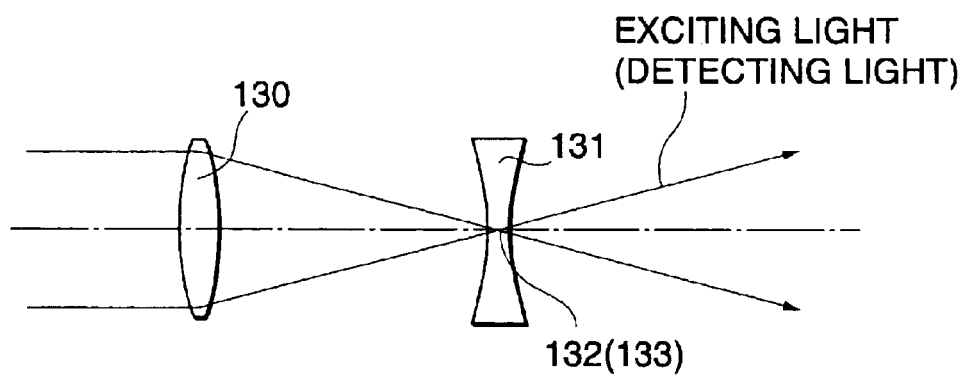
Figure 9A:
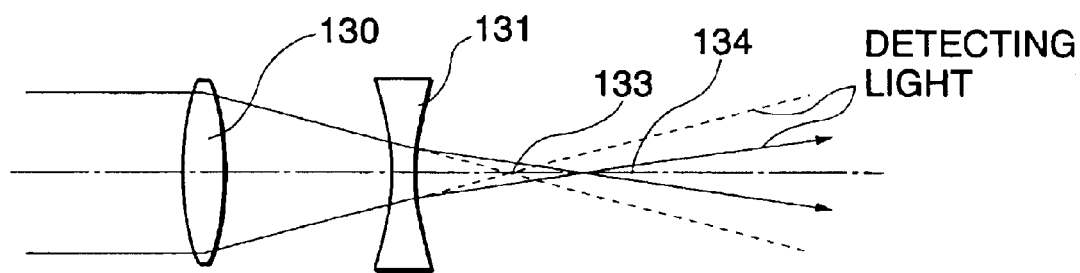
FIGS. 9A and 9B are views useful in explaining the formation position of a thermal lens and the focal position of detecting light in the direction of travel of exciting light; specifically.
Figure 9B:
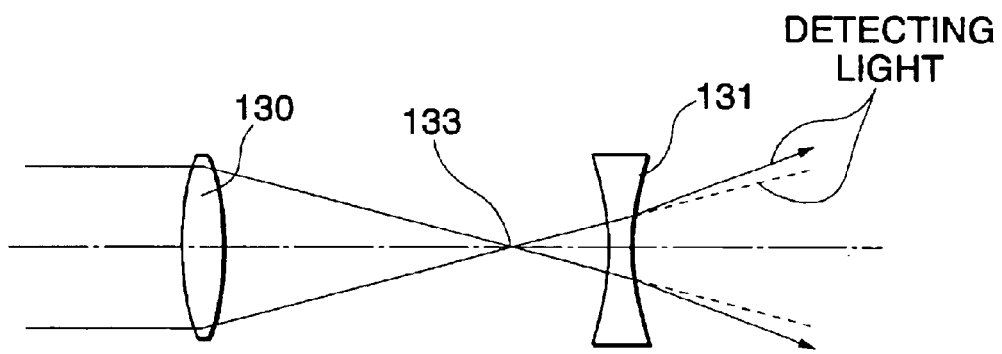
Figure 10:
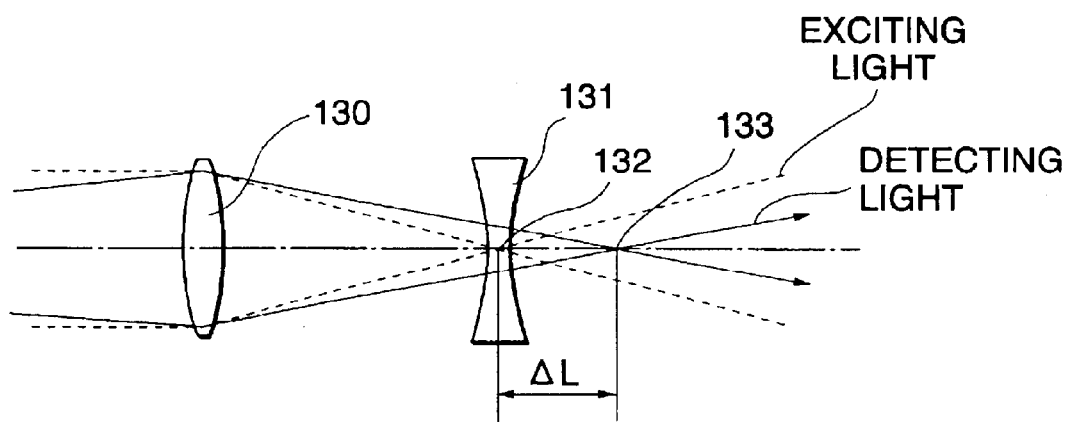
FIG. 10 is a view useful in explaining a method of detecting changes in refractive index within a thermal lens in a conventional photothermal conversion spectroscopic analyzer in the case that the detecting light is diverged using a diverging lens.

The rod lens 102 is designed such that the focal position of the detecting light is shifted slightly by an amount ΔL relative to the focal position of the exciting light (see FIG. 8A).

The confocal length Ic (nm) is given by $Ic=\pi\cdot(d/2)^2/\lambda_1$, wherein d represents the diameter of the Airy disk and is given by $d=1.22\times\lambda_1/NA$, $\lambda_1$ represents the wavelength (nm) of the exciting light, and NA represents the numerical aperture of the rod lens 102. When an optical fiber is used, the numeral aperture of output light of the optical fiber is small, and therefore, if a rod lens having a large numerical aperture is used, calculations must be carried out using the numerical aperture of the optical fiber.

The $\Delta L$ value described above varies according to the thickness of the sample to be analyzed. When carrying out measurements on a sample having a thickness lower than the confocal length, it is most preferable for $\Delta L$ to be equal to $\sqrt{3} \cdot lc$.

Figure 2:
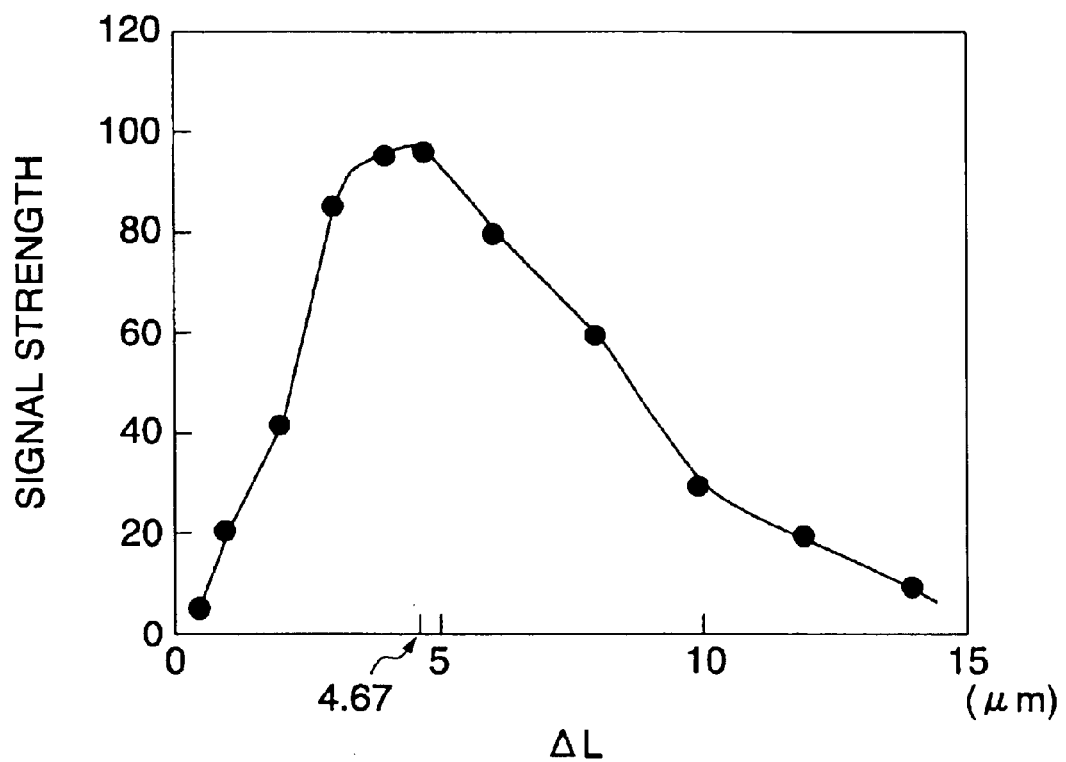
FIG. 2 is a graph useful in explaining the change in signal strength relative to the shift ΔL from the optimum focal position of a rod lens 10 appearing in FIG. 1.

For example, if NA=0.46, $\lambda_1$=488 nm and $\lambda_2$=632.8 nm, then the relationship between the value of the shift (L and the signal strength is as shown in FIG. 2. FIG. 2 shows the signal strength relative to the value at $\Delta L$=4.67 μm, with the value at ($\Delta L$=4.67(m being taken to be 100. It can be seen that the signal strength is a maximum at $\Delta L$=4.67 μm. In this case, it is thus preferable to design the rod lens 102 such that the shift $\Delta L$ is the optimum value of 4.67 μm. $\Delta L$ merely represents the difference between the focal position of the detecting light and the focal position of the exciting light, and the same result is achieved regardless of whether the focal distance of the detecting light is longer or shorter than the focal distance of the exciting light.

The reason why the optical fiber 101 is of the single mode type is that in the case where a very small amount of solute in a sample is detected using the photothermal conversion spectroscopic analysis method, it is desirable that the exciting light should be as small as possible to obtain a great amount of energy used for the photothermal conversion, and a thermal lens having a small aberration should be generated by the exciting light. The exciting light used to generate the thermal lens should desirably have a Gaussian distribution. Since light output from an optical fiber of the single mode type always has a Gaussian distribution, such an optical fiber is suitable for making the focal point of the exciting light small. If the thermal lens generated by the exciting light is small in size, it is desirable that the detecting light should also be limited to as small in diameter as possible to increase the number of detecting light beams passing the thermal lens to the maximum possible number. To this end, it is preferable to use an optical fiber in which the exciting light and the detecting light are transmitted in the single mode.

It should be noted that any type of optical fiber can be employed insofar as it can transmit the exciting light and the detecting light. However, if a multiple mode optical fiber is employed, output light from the optical fiber does not have a Gaussian distribution and the output light pattern varies depending on various conditions such as the manner of bending of the optical fiber, which does not always lead to stable output light being obtained. This is why measurement of a very small amount of solute is difficult to perform and the measurement result is inaccurate. Thus, it is preferable to employ an optical fiber of the single mode type as mentioned above.

If the tip of the optical fiber is machined to a sphere or the like, the diameters of the exciting light and the detecting light can be made small even if a lens is not mounted on the tip of the optical fiber. In this case, however, since the lens section has almost no aberration, the exciting light and the detecting light have almost the same focal position. Therefore, almost no signal from the thermal lens can be detected. Further, the lens formed by machining the tip of the optical fiber has a large aberration, which results in large focal point diameters of the exciting light and the detecting light. For these reasons, in the present embodiment, the lens 102 is mounted on the tip of the optical fiber 101.

Figure 3:
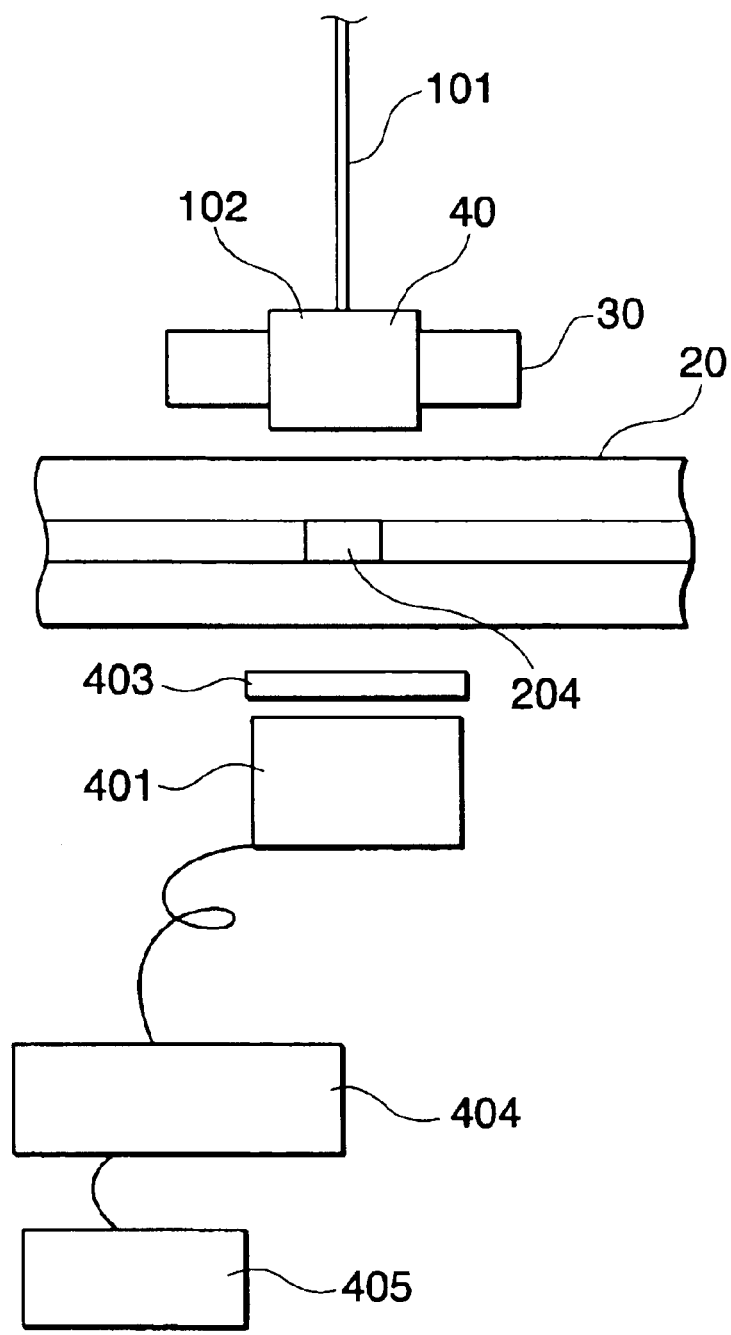
FIG. 3 is a schematic view showing the constitution of a microchemical system according to a second embodiment of the present invention.

FIG. 3 is a schematic view showing the constitution of a microchemical system according to a second embodiment of the present invention.

An optical fiber 40 is comprised of an optical fiber 101 and a gradient index rod lens 102 which are joined together by an adhesive or thermal bonding. The same adhesive as used in the above-described channel-formed plate-shaped element 20 may be used to join together these members.

As is distinct from the microchemical system according to the first embodiment of the present invention, the ferrule 103 and the sleeve 104 are not used. Thus, the present microchemical system can be lower in cost and designed more compact in size as compared with the microchemical system shown in FIG. 1.

It should be noted that, by designing such that the side of the optical fiber 101 on which the gradient index rod lens 102 is mounted (light inputting optical system) can be moved by means of a jig, any desired portion of a sample can be measured. If it is designed such that the channel-formed plate-shaped element 20 can be moved so as to change the measuring point, the flow of the sample in the channel 204 can become turbulent to affect the reaction and the like. If measurement is carried out after a turbulence disappears, it will result in degraded working efficiency. These inconveniences never occur in the case where the optical fiber 40 side is moved.

Figure 4:
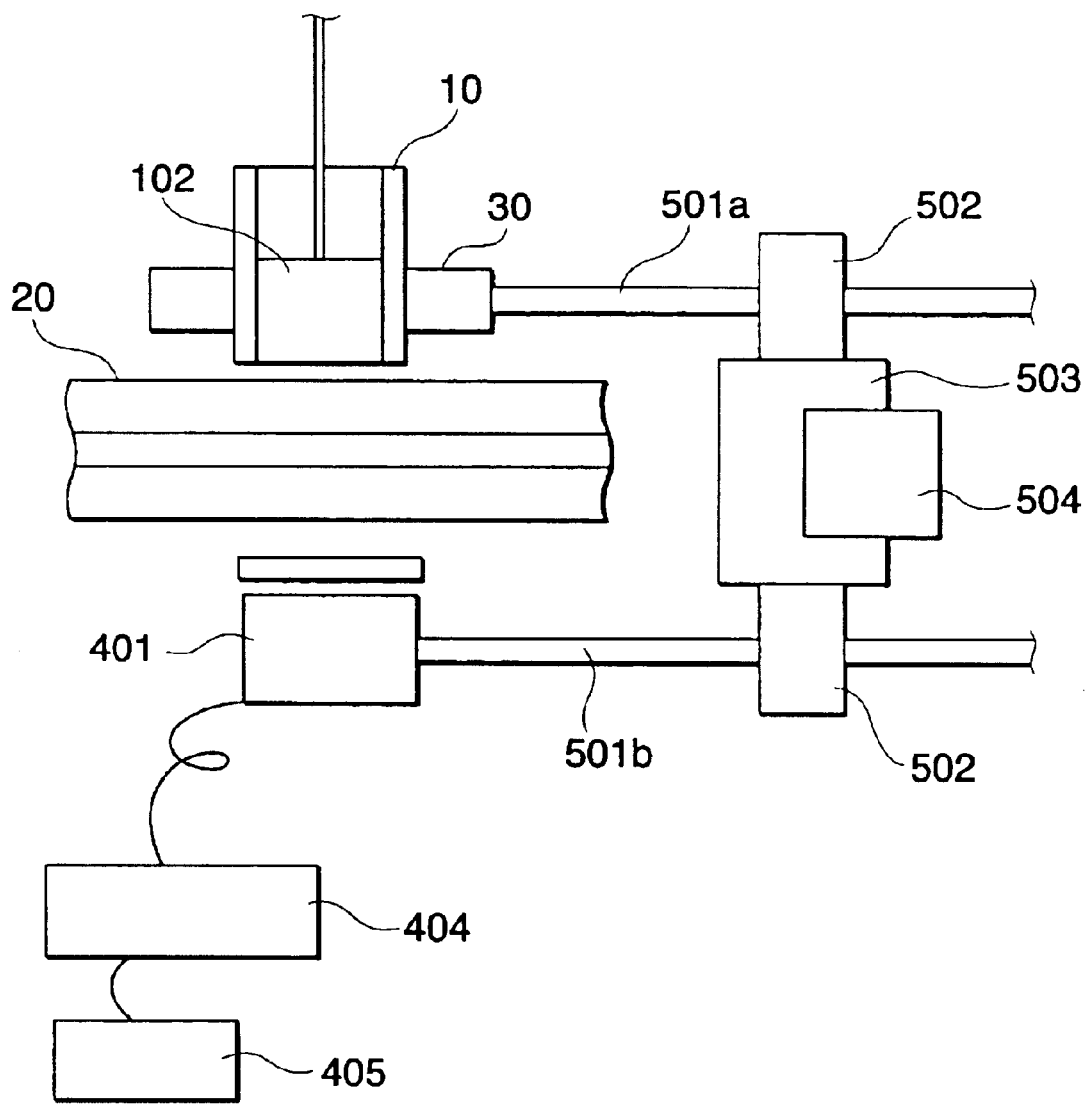
FIG. 4 is a schematic view showing the constitution of a microchemical system according to a third embodiment of the present invention.

FIG. 4 is a schematic view showing the constitution of a microchemical system according to a third embodiment of the present invention.

An optical fiber 10 has a lens 102 mounted on a tip thereof (lens-possessing optical fiber 10), as is the case with the microchemical system according to the first embodiment of the present invention. A jig 30 to which the lens-possessing optical fiber 10 is secured is supported by a support member 501a. The support member 501a is disposed above a channel-formed plate-shaped element 20 and extends parallel with a direction in which the major surface of the channel-formed plate-shaped element 20 extends. At a location below the channel-formed plate-shaped element 20, a support member 501b is disposed and extends parallel with the support member 501a. The support member 501b supports a photoelectric transducer 401 and a wavelength filter 402. The support members 501a, 501b are supported by a stage 502. The stage 502 controls the feed amounts of the support members 501a, 501b to control the positions of the lens-possessing optical fiber 10 and the photoelectric transducer 401 in a Y-axis direction (the horizontal direction as viewed in FIG. 4). The stage 502 is supported by a stage 503 which is moveable in an X-axis direction (the vertical direction as viewed in FIG. 4). With this arrangement, the positions of the lens-possessing optical fiber 10 and the photoelectric transducer 401 can be moved in the X-axis and Y-axis directions as desired by controlling the support members 501a, 501b and the stage 502. It should be noted that the support members 501a, 501b may be fixed to a simple XY stage which is available on the market.

To evaluate a thermal lens formed by exciting light irradiated onto a sample, it is required to measure changes in the intensity of detecting light passing through the sample due to deflection thereof. To this end, when the measuring position is moved by moving the irradiation positions of the exciting light and the detecting light, the photoelectric transducer 401 and the wavelength filter 402 have to be moved accordingly. This movement is carried out by the above-described arrangement.

Figure 5:
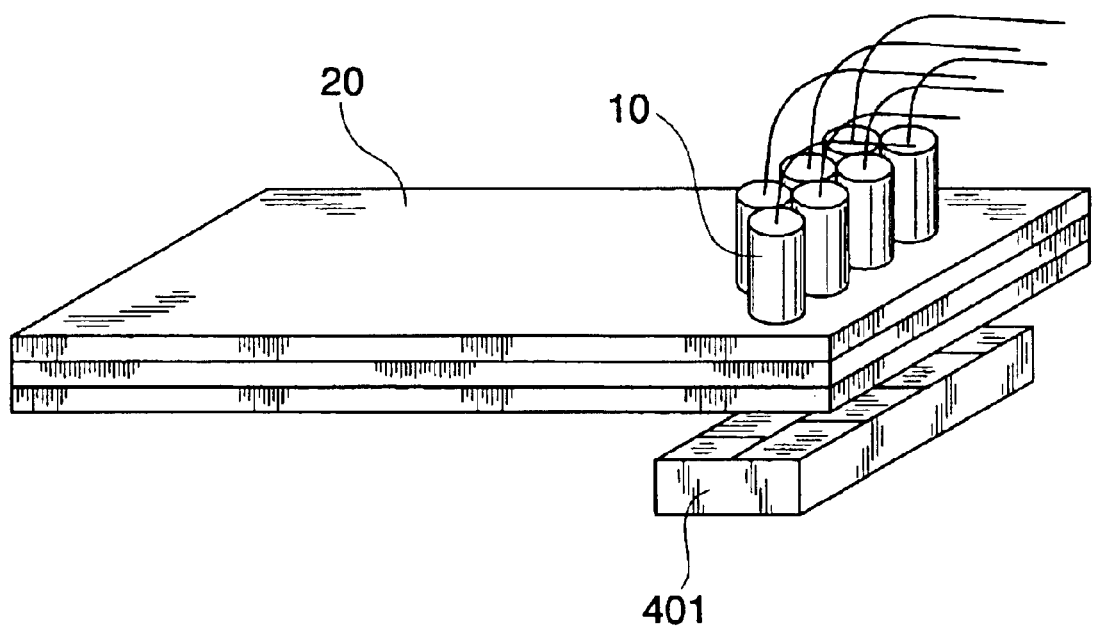
FIG. 5 is a schematic fragmentary perspective view showing the constitution of a microchemical system according to a fourth embodiment of the present invention.

FIG. 5 is a fragmentary perspective view showing essential parts of a microchemical system according to a fourth embodiment of the present invention.

In FIG. 5, a plurality of lens-possessing optical fibers 10 each having the same construction with that in FIG. 1 are used. A plurality of photoelectric transducers 401 and a plurality of wavelength filters (not shown) are arranged in pairs with respective ones of the optical fibers 10. The photoelectric transducers 401 may be in separate bodies from the respective optical fibers 10 or may be connected to the optical fibers in the form of an array.

In the microchemical system in which a plurality of lens-possessing optical fibers 10 are thus arranged, an exciting light source and a detecting light source may be provided for each lens-possessing optical fiber 10, or a single pair of exciting light source and a detecting light source may be switched by a switch, not shown, to be used with selected ones of the lens-possessing optical fibers 10.

By thus arranging a plurality of lens-possessing optical fibers on a sample, measurements can be performed at many measuring points. In this case, a mechanism or means for moving the lens-possessing optical fibers is not required, whereby the microchemical system can be designed more compact in size, and the measuring point can be changed to another measuring point for measurement without moving the lens-possessing optical fiber 10, making it possible to achieve prompt measurement and hence improve the working efficiency of the user.

Figure 6:
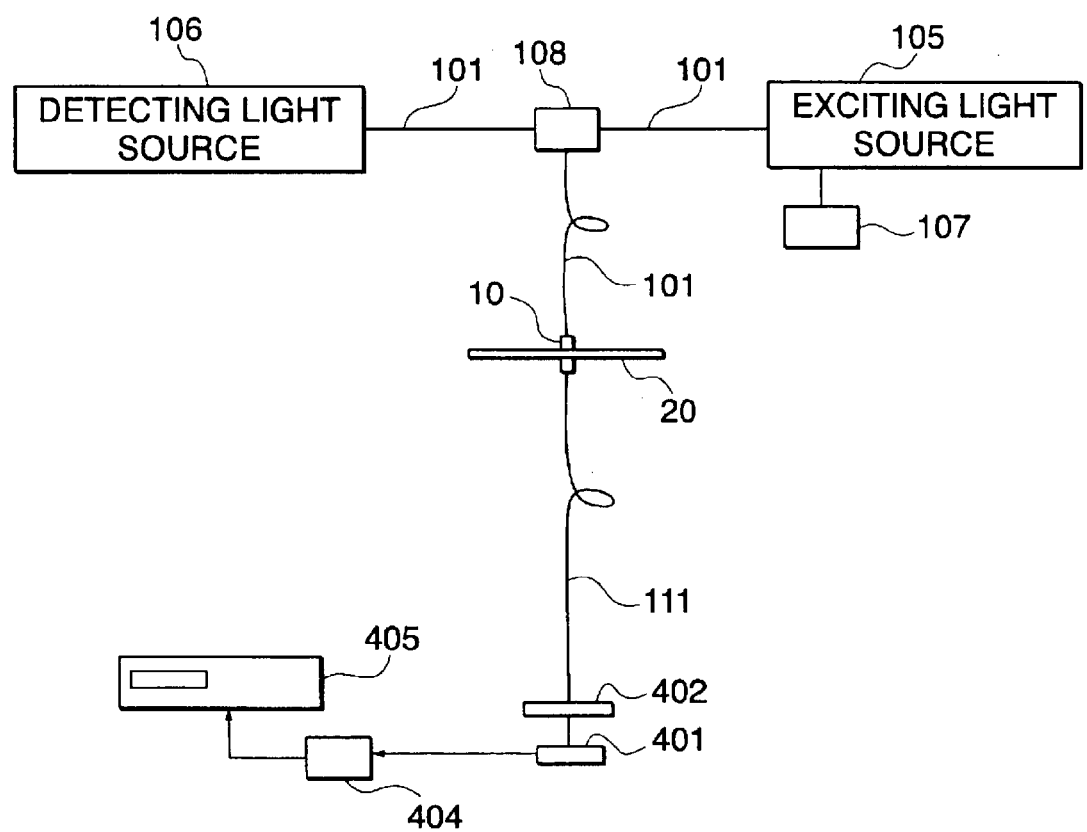
FIG. 6 is a schematic view showing the constitution of a microchemical system according to a fifth embodiment of the present invention.
Figure 7:
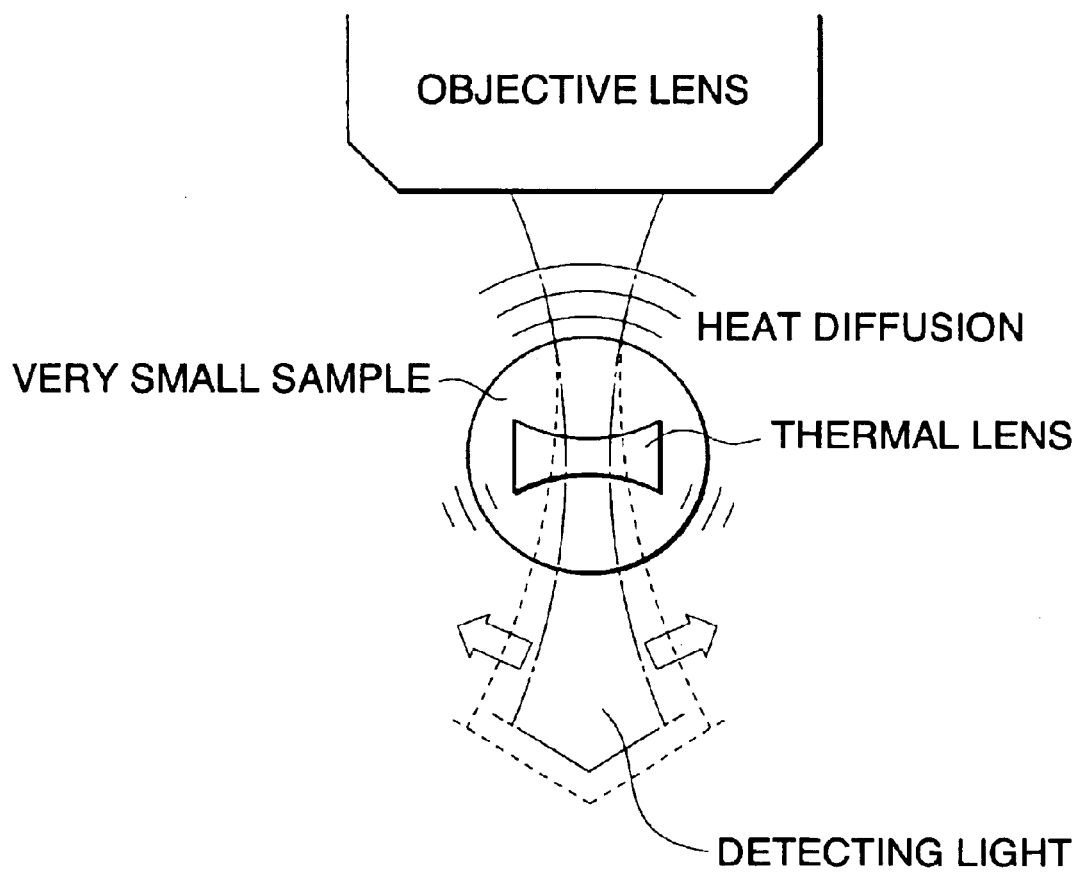
FIG. 7 is a view useful in explaining the principle of a thermal lens.

FIG. 6 is a schematic view showing the constitution of a microchemical system according to a fifth embodiment of the present invention.

The microchemical system according to the present embodiment is distinguished from the microchemical system according to the first embodiment in that a lens-possessing optical fiber 10 is fixed to a channel-formed plate-shaped element 20, and an optical fiber 111 is also provided in a light outputting optical system that guides detecting light passing through the channel-formed plate-shaped element 20.

According to the microchemical system of the present embodiment, since the lens-possessing optical fiber 10 is fixed to the channel-formed plate-shaped element 20, it is not necessary to adjust the focal position and measuring position each time measurement is carried out. Therefore, no mechanism or means for adjusting the focal position and measuring position is required, to thereby enable designing the microchemical system compact in size.

Further, since the optical fiber 111 is used in the light outputting optical system, a detector can be installed at a remote place from the channel-formed plate-shaped element 20, to thereby enable designing the microchemical system compact in size. As the optical fiber for use in the light outputting optical system, any type of optical fiber may be used insofar as it can pass the detecting light.

According to the microchemical systems of the above embodiments, it is not necessary to align the optical paths for the exciting light and the detecting light with the optical axis of the lens. Further, measurements can be performed at a plurality of locations in the channel-formed plate-shaped element without moving the channel-formed plate-shaped element, whereby the microchemical systems are free of the inconvenience that measurements have to be suspended until turbulence of a sample in the channel disappears. As a result, the working efficiency of the user can be improved.

Moreover, an objective lens and a condenser lens as employed in microscopes and the like are not required for convergent irradiation of light onto the channel-formed plate-shaped element, which also makes it possible to design the system compact in size.

INDUSTRIAL APPLICABILITY

As described above in detail, according to the present invention, the microchemical system is provided with an optical fiber for guiding the exciting light and the detecting light to the sample. Therefore, it is not necessary to adjust the optical paths for the exciting light and the detecting light for each measurement, whereby the working efficiency of the user can be improved, and further, no jig is required to align the optical paths, whereby the microchemical system can be designed compact in size According to the present invention, a converging lens is secured to one of both ends of the optical fiber that is closer to the sample. Therefore, it is not necessary to make adjustment so as to align the exciting light and the detecting light with the optical axis of the converging lens for each measurement, whereby the working efficiency of the user can be improved.

According to the present invention, the optical fiber comprises a single optical fiber. As a result, the exciting light and the detecting light are always coaxially aligned with each other, whereby no jig for adjusting the optical axis is required, to thereby enable designing the microchemical system more compact in size.

According to the present invention, the exciting light and the detecting light have respective different frequencies, the converging lens has chromatic aberration, and the exciting light and the detecting light passing through the converging lens have respective different focal positions. As a result, a change in the thermal lens can always be detected from a change in the focal position of the detecting light, whereby measurement of the sample can be always measured with accuracy.

According to the present invention, the converging lens is a gradient index lens. Therefore, the converging lens can be made very compact in size, to enable designing the microchemical system more compact in size.

According to the present invention, the gradient index lens is a rod lens. The rod lens can be easily attached to the optical fiber, and therefore the optical axis of the rod lens can be easily aligned with the optical axis of the optical fiber.

According to the present invention, the optical fiber exhibits a single mode in the frequencies of the exciting light and the detecting light. As a result, a thermal lens generated by the exciting lens has small aberration, making it possible to achieve more accurate measurement.

According to the present invention, the microchemical system comprises moving means for moving the optical fiber having the converging lens secured to the one end thereof. Therefore, any desired location in the sample can be measured by moving the converging lens together with the optical fiber, and in addition, the sample side is not moved, which makes it unnecessary to wait until a turbulence in the flow of the sample due to movement of the same disappears, and hence further improve the working efficiency of the user.

According to the present invention, the microchemical system comprises at least two pairs of the optical fiber and the converging lens secured to the one end of the optical fiber. As a result, at least two locations in the sample can be promptly measured, further improving the working efficiency of the user.

What is claimed is:

1. A microchemical system comprising:
    a channel for holding a fluid sample;
    a converging lens for convergently irradiating exciting light and detecting light onto the fluid sample such that a focal position of the exciting light is located in the channel;
    an optical fiber for guiding the exciting light and the detecting light to the converging lens;

a modulator for modulating the exciting light;

a single detector paired with the converging lens to detect the detecting light after the detecting light passes through a thermal lens generated in the fluid sample by the convergent irradiation of the exciting light; and a synchronizing device which synchronizes an output signal of the detector with the modulation of the exciting light by the modulator.

2. The microchemical system as claimed in claim 1, wherein the converging lens is secured to an end of the optical fiber that is closer to the sample.

3. The microchemical system as claimed in claim 2, wherein the optic fiber comprises a single optical fiber.

4. A microchemical system as claimed in claim 2, or 3, wherein the exciting light and the detecting light have respective different frequencies, the converging lens has chromatic aberration, and the exciting light and the detecting light passing through the converging lens have respective different focal positions.

5. The microchemical system as claimed in any one of claims 1 to 3, wherein the converging lens comprises a gradient index lens.

6. The microchemieal system as claimed in claim 5, wherein the gradient index lens comprises a rod lens.

7. The microchemical system as claimed in any one of claims 1 to 3, wherein the optical fiber exhibits a single mode in frequencies of the exciting light and the detecting light.

8. The microchemical system as claimed in claim 2 or 3, further comprising moving means for moving the optical fiber having the converging lens secured to the one end thereof in a direction parallel to a channel-formed element in which the channel is formed.

9. The microchemical system as claimed in claim 2, wherein the system comprises at least two converging lenses, each secured to a corresponding optical fiber.

10. The microchemical system as claimed in claim 4, wherein the converging lens comprises a gradient index lens.

11. The microchemical system as claimed in claim 1, further comprising a channel-formed element in which the channel is formed;

wherein the converging lens fixed in opposed relation to the channel-formed element.

12. The microchemical system as claimed in claim 11, wherein the converging lens is fixed in contact with the channel-formed element.

* * * * *